United States Patent
Andre et al.

(10) Patent No.: US 8,057,815 B2
(45) Date of Patent: Nov. 15, 2011

(54) METHODS OF TREATMENT WITH SYK INHIBITORS

(75) Inventors: Patrick Andre, San Mateo, CA (US);
David R. Phillips, San Mateo, CA (US);
Charles Homcy, San Francisco, CA (US)

(73) Assignee: Portola Pharmaceuticals, Inc., South San Francisco, CA (US)

( * ) Notice: Subject to any disclaimer, the term of this patent is extended or adjusted under 35 U.S.C. 154(b) by 1626 days.

(21) Appl. No.: 11/107,324

(22) Filed: Apr. 15, 2005

(65) Prior Publication Data
US 2005/0232969 A1 Oct. 20, 2005

Related U.S. Application Data

(60) Provisional application No. 60/563,710, filed on Apr. 19, 2004.

(51) Int. Cl.
*A61F 2/02* (2006.01)

(52) U.S. Cl. ............................................. 424/423
(58) Field of Classification Search ................ None
See application file for complete search history.

(56) References Cited

U.S. PATENT DOCUMENTS 5,171,217 A    12/1992  March et al.
2005/0181008 A1*  8/2005  Hunter et al. ............. 424/423

* cited by examiner

*Primary Examiner* — Carlos Azpuru
(74) *Attorney, Agent, or Firm* — Kilpatrick Townsend and Stockton LLP

(57) ABSTRACT

The present invention provides novel compositions and methods for inhibiting restenosis, thrombosis, and/or inflammation in a patient undergoing a vascular intervention. More particularly, the present invention provides intravascular devices coated with one or more spleen tyrosine kinase (Syk) inhibitors. Methods for inhibiting restenosis, thrombosis, and/or inflammation in a patient by treatment with such intravascular devices are also provided. In addition, the present invention provides methods for treating sickle cell disease using Syk inhibitors.

13 Claims, 4 Drawing Sheets

METHODS OF TREATMENT WITH SYK INHIBITORS

CROSS-REFERENCES TO RELATED APPLICATIONS

The present application claims priority to U.S. Provisional Application No. 60/563,710, filed Apr. 19, 2004, which is herein incorporated by reference in its entirety for all purposes.

BACKGROUND OF THE INVENTION

Arteriosclerosis is a class of diseases characterized by the thickening and hardening of the arterial walls of blood vessels. Although all blood vessels are susceptible to this serious degenerative condition, the aorta and the coronary arteries serving the heart are most often affected. Arteriosclerosis is of profound clinical importance since it can increase the risk of heart attacks, myocardial infarctions, strokes, and aneurysms.

The traditional treatment for arteriosclerosis includes vascular recanalization procedures for less-serious blockages and coronary bypass surgery for major blockages. Where possible, vascular recanalization is much preferred to coronary bypass because it is a far less invasive procedure. Vascular recanalization procedures involve using intravascular devices threaded through blood vessels to the obstructed site, and include, for example, percutaneous transluminal coronary balloon angioplasty (PTCA), also known as balloon angioplasty, and stents. Balloon angioplasty uses a catheter with a balloon tightly packed onto its tip. When the catheter reaches the obstruction, the balloon is inflated, causing the atherosclerotic plaques to become compressed against the vessel wall, and resulting in improved blood flow. However, a serious shortcoming of this and other intravascular procedures is that, in a significant number of treated individuals, some or all of the treated vessels restenose (i.e., re-narrow). For example, restenosis of an atherosclerotic coronary artery after PTCA occurs in 10-50% of patients undergoing this procedure and subsequently requires either further angioplasty or a coronary artery bypass graft. Furthermore, restenosis of an atherosclerotic coronary artery after stenting occurs in 10-20% of patients undergoing this procedure and subsequently requires repeat treatments to maintain adequate blood flow through the affected artery. Restenosis generally occurs in a relatively brief time period, e.g., roughly less than six months, after treatment.

While the exact hormonal and cellular processes promoting restenosis have not been determined, restenosis is thought to be due in part to mechanical injury to the walls of the blood vessels caused by the balloon catheter or other intravascular device. For example, the process of PTCA, in addition to opening the obstructed artery, also injures resident coronary arterial smooth muscle cells (SMCs). In response to this injury, adhering platelets, infiltrating macrophages, leukocytes, or the smooth muscle cells themselves release cell-derived growth factors such as platelet-derived growth factor (PDGF), with subsequent proliferation and migration of medial SMCs through the internal elastic lamina to the area of the vessel intima. Further proliferation and hyperplasia of intimal SMCs and, most significantly, production of large amounts of extracellular matrix over a period of three to six months results in the filling in and narrowing of the vascular space sufficient to significantly obstruct blood flow.

Several methods for inhibiting SMC proliferation following the use of an intravascular device have been reported in the patent literature. These include, for example, the local or systemic administration of anti-proliferative agents such as cell cycle inhibitors and anti-coagulant agents. However, systemic delivery of these agents requires doses that cause unacceptable side-effects or are prohibitively expensive. In addition, local delivery of agents such as heparin, as described in U.S. Pat. No. 4,824,436, has proven ineffective in inhibiting restenosis due in part to inadequate residence time of heparin at the site of injury. Cell cycle inhibitors such as taxol, which do not react covalently and therefore require prolonged residence time for effectiveness, suffer from similar problems. Moreover, prolonging residence times to increase the effectiveness of such treatments is also likely to present increased risks of toxicity.

Other methods reported for inhibiting SMC proliferation involve local delivery of active agents contained in a sustained-release formulation. For example, U.S. Pat. No. 5,171,217 describes active agents contained within a physiologically compatible, biodegradable polymeric microparticle. This formulation is delivered locally to the site of injury such that the agents are released from the arterial wall for 72 hours or more. An additional method for inhibiting SMC proliferation involves administering photochemically-activated agents by local delivery systems. For example, U.S. Pat. No. 5,354,774 describes locally delivering 8-methoxypsoralen to the site of injury and then activating a photodynamic reaction using a visible light source. Yet another approach for preventing SMC proliferation involves the use of radiation-emitting catheters or guide-wires. The radiation causes damage to the nucleic acid within SMCs, thereby inhibiting DNA replication and smooth muscle cell proliferation.

However, all of the above-described methods suffer from certain significant drawbacks. For example, sustained release formulations require the incorporation of the active agent within a sustained release formulation. Photodynamic therapy requires both local delivery of the photo-active agent and the use of a complex intravascular light source. Delivery of a radiation dose requires the presence of a radiologist and presents exposure hazards to the attending personnel, as well as material storage, handling, and disposal complications.

A significant drawback to the uncoated and drug-coated coronary stents now on the market or in clinical trials lies in their failure to inhibit thrombosis in the vicinity of the deployed stent. For example, thrombosis has been observed in human clinical trials when using stents coated with either taxol or rapamycin. To prevent such thrombosis, patients have had to undergo anti-coagulation treatment for a two- to three-month duration. Another significant drawback is that inflammation still occurs following stent placement.

Thus, there is a need to develop a safe and effective intravascular device for inhibiting restenosis, thrombosis, and/or inflammation in a patient following vascular intervention with the device. The present invention satisfies this and other needs.

BRIEF SUMMARY OF THE INVENTION

The present invention provides novel compositions and methods for inhibiting restenosis, thrombosis, and/or inflammation in a patient undergoing a vascular intervention. More particularly, the present invention provides intravascular devices coated with one or more spleen tyrosine kinase (Syk) inhibitors. Methods for inhibiting restenosis, thrombosis, and/or inflammation in a patient by treatment with such intravascular devices are also provided. In addition, the present invention provides methods for treating sickle cell disease using Syk inhibitors.

As such, in one aspect, the present invention provides an intravascular device having a coating, the coating comprising a polymer and a spleen tyrosine kinase (Syk) inhibitor, wherein the coating is applied to the intravascular device.

In another aspect, the present invention provides a method for inhibiting restenosis in a patient undergoing a vascular intervention, the method comprising:

treating the patient with an intravascular device having a coating, the coating comprising a polymer and a Syk inhibitor, wherein the coating is applied to the intravascular device.

In yet another aspect, the present invention provides a method for inhibiting restenosis, thrombosis, and inflammation in a patient undergoing a vascular intervention, the method comprising:

treating the patient with an intravascular device having a coating, the coating comprising a polymer and a Syk inhibitor, wherein the coating is applied to the intravascular device.

In still yet another aspect, the present invention provides a method for treating sickle cell disease in a patient in need thereof, the method comprising:

administering to the patient a therapeutically effective amount of a Syk inhibitor.

Other objects, features, and advantages of the present invention will be apparent to one of skill in the art from the following detailed description and figures.

DETAILED DESCRIPTION OF THE INVENTION

As used herein, the following terms have the meanings ascribed to them unless specified otherwise.

The term "restenosis" refers to a re-narrowing or blockage of an artery at the same site where treatment, such as an angioplasty or a stent procedure, has been performed.

The term "thrombosis" refers to the blockage or clotting of a blood vessel caused by a clumping of cells, resulting in the obstruction of blood flow. The term "thrombus" refers to the clot that is formed within the blood vessel.

The term "inflammation" as used herein refers to infiltration of white blood cells (e.g., leukocytes, monocytes, etc.) into the area being treated for restenosis.

The term "vessel" refers to any channel for carrying a fluid, such as an artery or vein. For example, a "blood vessel" refers to any of the vessels through which blood circulates in the body. The lumen of a blood vessel refers to the inner open space or cavity of the blood vessel.

The term "intravascular device" refers to a device useful for a vascular recanalization procedure to restore blood flow through an obstructed blood vessel. Examples of intravascular devices include, without limitation, stents, balloon catheters, autologous venous/arterial grafts, prosthetic venous/arterial grafts, vascular catheters, and vascular shunts.

The term "stent" refers to an expandable, slotted metal tube that is inserted into a vessel. The stent acts as a scaffold to provide structural support for the vessel, holding the vessel open and improving blood flow through the vessel. There are two categories of stents: uncoated stents and drug-coated stents.

As used herein, an "uncoated stent" refers to a stent that has not been coated with a drug. On the other hand, a "drug-coated stent" refers to a stent that has been coated with a drug. The term "drug-eluting stent" refers to a drug-coated stent where the drug is placed on the stent using a process that allows the drug to be released over time into surrounding tissue. Preferably, the drug is a Syk inhibitor. However, one skilled in the art understands that the stent can be also be adsorbed to, impregnated with, covalently attached to, or ionically bonded to the drug.

The term "platelet" refers to a minute, nonnucleated, disklike cell found in the blood plasma of mammals that functions to promote blood clotting.

The term "leukocyte" refers to any of the various blood cells that have a nucleus and cytoplasm, separate into a thin white layer when whole blood is centrifuged, and help protect the body from infection and disease. Examples of leukocytes include, without limitation, neutrophils, eosinophils, basophils, lymphocytes, and monocytes.

The term "intervention" refers to an action that produces an effect or that is intended to alter the course of a disease process. For example, "vascular intervention" refers to the use of an intravascular procedure such as angioplasty or a stent to open an obstructed blood vessel.

The term "recanalization" refers to the process of restoring flow to or reuniting an interrupted channel of the body, such as a blood vessel.

The term "Syk inhibitor" refers to any agent that inhibits the catalytic activity of the Syk protein tyrosine kinase.

The term "sickle cell disease" refers to an inherited disorder of the red blood cells in which one hemoglobin allele encodes the sickle hemoglobin (S) protein, and the other allele encodes another unusual hemoglobin protein, such as hemoglobin (S), (C), (D), (E), and (βThal). Examples of sickle cell disease genotypes include, without limitation, the S/S, S/C, S/D, S/E, and S/βThal genotypes. The most common types of sickle cell disease include sickle cell anemia, sickle-hemoglobin C disease, sickle beta-plus thalassemia, and sickle beta-zero thalassemia.

As used herein, the term "sickle cell anemia" refers to an inherited disorder of the red blood cells in which both hemoglobin alleles encode the sickle hemoglobin (S) protein, i.e., the S/S genotype. The presence of abnormal hemoglobin results in the production of unusually shaped cells, which do not survive the usual length of time in the blood circulation. Thus, anemia results. "Anemia" refers to a decrease in the number of red blood cells and/or hemoglobin in the blood.

The term "administering" refers to oral administration, administration as a suppository, topical contact, intravenous, intraperitoneal, intramuscular, intralesional, intranasal or subcutaneous administration, or the implantation of a slow-release device e.g., a mini-osmotic pump, to a subject. Adminsitration is by any route, including parenteral and transmucosal (e.g., buccal, sublingual, palatal, gingival, nasal, vaginal, rectal, or transdermal). Parenteral administration includes, e.g., intravenous, intramuscular, intra-arteriole, intradermal, subcutaneous, intraperitoneal, intraventricular, and intracranial. Other modes of delivery include, but are not limited to, the use of liposomal formulations, intravenous infusion, transdermal patches, etc.

II. GENERAL OVERVIEW

The present invention provides novel compositions and methods for inhibiting restenosis, thrombosis, and/or inflammation in a patient undergoing a vascular intervention. Specifically, the present invention provides intravascular devices coated with one or more spleen tyrosine kinase (Syk) inhibitors. Methods for inhibiting restenosis, thrombosis, and/or inflammation in a patient by treatment with such intravascular devices are also provided. In addition, the present invention provides methods for treating sickle cell disease using Syk inhibitors.

The present invention is based upon the surprising discovery that the Syk inhibitors according to the present invention function by blocking the adhesion of platelets and leukocytes at the site of vascular intervention. The adhesion of platelets and leukocytes causes thrombosis and restenosis, respectively. As a result, the present invention provides a drug-eluting stent with a Syk inhibitor coated thereon for the sustained release of the Syk inhibitor effective to inhibit both platelet thrombotic activity and restenosis caused by leukocyte recruitment. Thus, the failure of currently available uncoated and drug-coated stents to inhibit both restenosis and thrombosis in a patient following vascular intervention is overcome with the compositions and methods of the present invention.

The present invention is also based upon the surprising discovery that the Syk inhibitors according to the present invention function by blocking the P-selectin-mediated adhesion of sickle cells to the vascular endothelium. The adhesion of sickle cells to endothelial cells is important to the generation of vascular occlusion and is mediated by cell adhesion molecules such as P-selectin. As a result, the present invention provides a method for treating sickle cell disease in a patient by administering a composition comprising a therapeutically effective amount of a Syk inhibitor. Thus, crises in patients with sickle cell disease brought about by vascular occlusion due to the recruitment and adhesion of sickle cells to the vascular endothelium are overcome with the methods of the present invention.

III. DESCRIPTION OF THE EMBODIMENTS

As such, in one aspect, the present invention provides an intravascular device having a coating, the coating comprising a polymer and a spleen tyrosine kinase (Syk) inhibitor, wherein the coating is applied to the intravascular device.

In one embodiment, the intravascular device is selected from the group consisting of a stent, a balloon catheter, an autologous venous/arterial graft, a prosthetic venous/arterial graft, a vascular catheter, and a vascular shunt. In a preferred embodiment, the intravascular device is a stent.

A variety of Syk inhibitors are useful in the present invention. Examples of Syk inhibitors include, without limitation, NVP-QAB205; purine-2-benzamine derivatives such as those described in U.S. Pat. No. 6,589,950, hereby incorporated by reference herein; pyrimidine-5-carboxamide derivatives such as those described in PCT Publication No. WO 99/31073, hereby incorporated by reference herein; 1,6-naphthyridine derivatives such as those described in U.S. Patent Publication No. 2003/0229090, hereby incorporated by reference herein; BAY 61-3606; piceatannol; 3,4-dimethyl-10-(3-aminopropyl)-9-acridone oxalate); and combinations thereof.

In yet another embodiment, the polymer is selected from the group consisting of a bioabsorbable polymer, a biostable polymer, and combinations thereof. Suitable bioabsorbable polymers include, without limitation, aliphatic polyesters, poly(amino acids), poly(ether-ester) copolymers, polyalkylene oxalates, polyanhydrides, polysaccharides, polyamides, poly(iminocarbonates), polyorthoesters, polyoxaesters, polyamidoesters, polyoxaesters containing amido groups, polyphosphazenes, and combinations thereof. Suitable biostable polymers include, without limitation, polyurethanes, silicones, polymethacrylates, poly(ethylene-vinylacetates), polyesters, polyalkyl oxides, polyvinyl alcohols, polyethylene glycols, polyvinyl pyrrolidone, polyolefins, polyisobutylene and ethylene-α-olefin copolymers, acrylic polymers and copolymers, vinyl halide polymers and copolymers, polyvinyl ethers, polyvinylidene halides, polyacrylonitriles, polyvinyl ketones, polyvinyl aromatics, polyvinyl esters, copolymers of vinyl monomers, acrylonitrile-styrene copolymers, acrylonitrile-butadiene-styrene copolymers, ethylene-vinyl acetate copolymers, polyamides, alkyl resins, polycarbonates, polyoxymethylenes, polyimides, polyethers, epoxy resins, rayon, rayon-triacetate, cellulose esters, cellulose acetate, cellulose acetate butyrate, cellophane, cellulose nitrate, cellulose propionate, cellulose ethers, and combinations thereof.

In certain instances, the Syk inhibitor is released from the intravascular device. In certain other instances, the Syk inhibitor is covalently attached to the intravascular device.

In still yet another embodiment, the coating contains one or more additional drugs. Suitable drugs include, without limitation, protein kinase inhibitors, antiproliferative agents, antimitotic agents, antibiotics, antimetabolites, pyrimidine analogs, purine analogs, anticoagulants, fibrinolytic agents, antiplatelet agents, antimigratory agents, antisecretory agents, anti-inflammatory agents, non-steroidal agents, immunosuppressive agents, angiogenic agents, and combinations thereof. In a preferred embodiment, the drug is an antibiotic such as rapamycin.

In certain instances, the coating is applied by dip coating. In certain other instances, the coating is applied by spray coating.

In another aspect, the present invention provides a method for inhibiting restenosis in a patient undergoing a vascular intervention, the method comprising:

treating the patient with an intravascular device having a coating, the coating comprising a polymer and a Syk inhibitor, wherein the coating is applied to the intravascular device.

In one embodiment, the intravascular device is selected from the group consisting of a stent, a balloon catheter, an autologous venous/arterial graft, a prosthetic venous/arterial graft, a vascular catheter, and a vascular shunt. Preferably, the intravascular device is a stent.

In another embodiment, the Syk inhibitor is selected from the group consisting of NVP-QAB205, purine-2-benzamine derivatives, pyrimidine-5-carboxamide derivatives, 1,6-naphthyridine derivatives, BAY 61-3606, piceatannol, 3,4-dimethyl-10-(3-aminopropyl)-9-acridone oxalate), and combinations thereof. Suitable polymers for use in the coatings of the present invention are described above.

In yet another aspect, the present invention provides a method for inhibiting restenosis, thrombosis, and inflammation in a patient undergoing a vascular intervention, the method comprising:

treating the patient with an intravascular device having a coating, the coating comprising a polymer and a Syk inhibitor, wherein the coating is applied to the intravascular device.

In one embodiment, the intravascular device is selected from the group consisting of a stent, a balloon catheter, an autologous venous/arterial graft, a prosthetic venous/arterial graft, a vascular catheter, and a vascular shunt. In a preferred embodiment, the intravascular device is a stent.

In another embodiment, the Syk inhibitor is selected from the group consisting of NVP-QAB205, purine-2-benzamine derivatives, pyrimidine-5-carboxamide derivatives, 1,6-naphthyridine derivatives, BAY 61-3606, piceatannol, 3,4-dimethyl-10-(3-aminopropyl)-9-acridone oxalate), and combinations thereof. Suitable polymers for use in the coatings of the present invention are described above.

In yet another embodiment, the Syk inhibitor blocks the adhesion of platelets to the lumen of a blood vessel. In still yet another embodiment, the Syk inhibitor blocks the adhesion of leukocytes to the lumen of a blood vessel. Without being bound to any particular theory, the Syk inhibitor blocks the adhesion of platelets by inhibiting their binding to collagen. Without being bound to any particular theory, the Syk inhibitor blocks the adhesion of leukocytes by inhibiting their binding to adhered platelets.

In a further aspect, the present invention provides a method for treating sickle cell disease in a patient in need thereof, the method comprising:

administering to the patient a therapeutically effective amount of a Syk inhibitor.

In one embodiment, the sickle cell disease is selected from the group consisting of sickle cell anemia, sickle-hemoglobin C disease, sickle beta-plus thalassemia, and sickle beta-zero thalassemia. In another embodiment, the Syk inhibitor is selected from the group consisting of NVP-QAB205, purine-2-benzamine derivatives, pyrimidine-5-carboxamide derivatives, 1,6-naphthyridine derivatives, BAY 61-3606, piceatannol, 3,4-dimethyl-10-(3-aminopropyl)-9-acridone oxalate), and combinations thereof.

IV. INTRAVASCULAR DEVICES

The present invention provides intravascular devices having a coating comprising a polymer and a Syk inhibitor which are useful for inhibiting restenosis, thrombosis, and/or inflammation in a patient undergoing a vascular intervention. Suitable intravascular devices include, without limitation, stents, balloon catheters, autologous venous/arterial grafts, prosthetic venous/arterial grafts, vascular catheters, and vascular shunts. Preferably, the intravascular device is a stent.

Stents generally fall into two categories: uncoated and drug-coated stents. Examples of drug-coated stents include, without limitation, drug-eluting stents and stents where drugs are adsorbed to, impregnated with, covalently attached to, or ionically bonded to the stents. Preferably, the stent is a drug-eluting stent where the drug, e.g., a Syk inhibitor, is placed on the stent using a process that allows the drug to be released over time into surrounding tissue. Additional drug-coated stents suitable for use in the present invention include, without limitation, stents where the drug is applied to the struts, grafts, cover, and/or sheath of the stent body, stents where the drug is embedded into the metal of the stent or graft body, and stents where the drug is placed in reservoirs, channels, or micropores on the stent body.

Stents are generally cylindrical and perforated with passages that are slots, ovoid, or circular in shape. Stents may also be composed of helically wound or serpentine wire structures in which the spaces between the wires form the passages. Stents may be flat perforated structures that are subsequently rolled to form tubular structures or cylindrical structures that are woven, wrapped, drilled, etched, or cut to form passages. Examples of stents that may be advantageously coated by the present process include, without limitation, stents described in the following: U.S. Pat. Nos. 4,733,665; 4,800,882; 4,886,062; and 5,514,154, incorporated by reference herein. These stents can be made of biocompatible materials including biostable and bioabsorbable materials. Suitable biocompatible metals include, but are not limited to, stainless steel, tantalum, titanium alloys (including nitinol), and cobalt alloys (including cobalt-chromium-nickel alloys). Suitable nonmetallic biocompatible materials include, but are not limited to, polyamides, polyolefins (e.g., polypropylene, polyethylene, etc.), nonabsorbable polyesters (e.g., polyethylene terephthalate), and bioabsorbable aliphatic polyesters (e.g., homopolymers and copolymers of lactic acid, glycolic acid, lactide, glycolide, para-dioxanone, trimethylene carbonate, $\epsilon$-caprolactone,etc., and blends thereof).

Typically, drug-eluting stents are prepared by coating the stent with a drug that has been incorporated into a polymer material. Preferably, the coating material adheres strongly to the metal stent both before and after expansion, is capable of retaining the drug at a sufficient load level to obtain the required dose, is able to release the drug in a controlled way over a period of several weeks, and is as thin as possible so as to minimize the increase in profile. In addition, the coating material should not contribute to any adverse response (e.g., thrombogenic, inflammatory, etc.) by the body. As such, suitable film-forming polymers that can be used as coating materials include both absorbable or non-absorbable polymers, and are preferably biocompatible (i.e., do not elicit any negative tissue reaction or promote mural thrombus formation) to minimize irritation to the vessel wall. The polymer can be biostable or bioabsorbable, depending on the desired rate of release or the desired degree of polymer stability, but a bioabsorbable polymer is preferred since, unlike a biostable polymer, it will not be present long after implantation to cause any adverse, chronic local responses. Furthermore, bioabsorbable polymers do not present the risk that, over extended periods of time, there could be an adhesion loss between the stent and coating caused by the stresses of the biological environment that could dislodge the coating and introduce further problems even after the stent is encapsulated in tissue.

Suitable bioabsorbable polymers that are useful coating materials in the present invention include, without limitation, polymers such as aliphatic polyesters, poly(amino acids), poly(ether-ester) copolymers (e.g., PEO-PLLA), polyalkylene oxalates, polyanhydrides, polysaccharides, polyamides, poly(iminocarbonates), polyorthoesters, polyoxaesters, polyamidoesters, polyoxaesters containing amido groups, polyphosphazenes, and combinations thereof. Examples of aliphatic polyesters include, without limitation, homopolymers and copolymers of lactide (e.g., lactic acid, D,L-lactide, L-lactide, and meso-lactide), F-caprolactone, glycolide (e.g., glycolic acid), hydroxybutyrate, hydroxyvalerate, para-dioxanone, trimethylene carbonate (and its alkyl derivatives), 1,4-dioxepan-2-one, 1,5-dioxepan-2-one, 6,6-dimethyl-1,4-dioxan-2-one, and polymer blends thereof.

Poly(iminocarbonates) generally include polymers such as those described by Kemnitzer and Kohn (*Handbook of Biodegradable Polymers*, Ed. Domb, Kost and Wisemen, Hardwood Academic Press, 251-272 (1997)). Poly(ether-ester) copolymers typicllay include polymers such as those described by Cohn et al. (*J. of Biomaterials Res.*, 22:993-1009 (1988)) and in *Polymer Preprints* (ACS Division of Polymer Chemistry, 30, 498 (1989)). Polyalkylene oxalates include polymers such as those described in U.S. Pat. Nos. 4,208,511; 4,141,087; 4,130,639; 4,140,678; 4,105,034; and 4,205,399, incorporated by reference herein. A variety of polyphosphazenes and polymers made from L-lactide, D,L-lactide, lactic acid, glycolide, glycolic acid, para-dioxanone, trimethylene carbonate and ε-caprolactone are also useful in the present invention and include polymers described by Allcock (*The Encyclopedia of Polymer Science*, Wiley Intersciences, John Wiley & Sons, 13:31-41 (1988)) and by Vandorpe et al. (*Handbook of Biodegradable Polymers*, Ed. Domb, Kost and Wisemen, Hardwood Academic Press, 161-182 (1997)), hereby incorporated by reference herein. Polyorthoesters generally include polymers such as those described by Heller (*Handbook of Biodegradable Polymers*, Ed. Domb, Kost and Wisemen, Hardwood Academic Press, 99-118 (1997)), hereby incorporated by reference herein. Examples of polymeric biomolecules include, without limitation, naturally-occurring materials that may be enzymatically degraded in the human body or are hydrolytically unstable in the human body such as fibrin, fibrinogen, collagen, elastin, and absorbable biocompatible polysaccharides such as chitosan, starch, fatty acids (and esters thereof), glucoso-glycans, hyaluronic acid, and combinations thereof.

Suitable biostable polymers that are useful coating materials in the present invention include, without limitation, polymers such as polyurethanes, silicones (e.g., polydimethylsiloxane), polymethacrylates, poly(ethylene-vingylacetates), polyesters, polyalkyl oxides (e.g., polyethylene oxide), polyvinyl alcohols, polyethylene glycols, fluorinated polymers (e.g., polytetrafluoroethylene), cellulose esters, and polyvinyl pyrrolidone; hydrogels such as those formed from crosslinked polyvinyl pyrrolidinone and polyesters; and combinations thereof. Other polymers suitable for use include polyolefins, polyisobutylene and ethylene-α-olefin copolymers, acrylic polymers (e.g., methacrylate) and copolymers, vinyl halide polymers and copolymers (e.g., polyvinyl chloride), polyvinyl ethers (e.g., polyvinyl methyl ether), polyvinylidene halides (e.g., polyvinylidene fluoride and polyvinylidene chloride), polyacrylonitriles, polyvinyl ketones, polyvinyl aromatics (e.g., polystyrene), polyvinyl esters (e.g., polyvinyl acetate), copolymers of vinyl monomers with each other and olefins (e.g., etheylene-methyl methacrylate copolymers), acrylonitrile-styrene copolymers, acrylonitrile-butadiene-styrene (ABS) copolymers, ethylene-vinyl acetate copolymers, polyamides (e.g., Nylon 66 and polycaprolactam), alkyl resins, polycarbonates, polyoxymethylenes, polyimides, polyethers, epoxy resins, rayon, rayon-triacetate, cellulose acetate, cellulose acetate butyrate, cellophane, cellulose nitrate, cellulose propionate, cellulose ethers (e.g., carboxymethyl cellulose and hydoxyalkyl celluloses), and combinations thereof.

The polymers used as coating materials should adhere to the stent and not be so readily deformable after deposition on the stent as to be able to be displaced by hemodynamic stresses. The molecular weight of the polymers should also be high enough to provide sufficient toughness so that the polymers are not rubbed off during handling or deployment of the stent and do not crack during expansion of the stent. The melting point of the polymer should have a melting temperature of above about 40° C., preferably above about 45° C., more preferably above about 50° C., and most preferably above about 55° C.

In a preferred embodiment of the present invention, the polymers used as coating materials are bioabsorbable elastomers, such as aliphatic polyester elastomers. Elastomers present the advantage in that they adhere well to the metal stents and can withstand significant deformation without cracking. Their high elongation and good adhesion properties provide superior performance to other polymer coatings when the coated stent is expanded. Examples of suitable bioabsorbable elastomers are described in U.S. Pat. No. 5,468,253, hereby incorporated by reference herein. The bioabsorbable elastomers should have an inherent viscosity of from about 1.0 dL/g to about 4 dL/g, preferably from about 1.0 dL/g to about 2 dL/g, and more preferably from about 1.2 dL/g to about 2 dL/g, as determined at 25° C. in a 0.1 gram per deciliter (g/dL) solution of polymer in hexafluoroisopropanol (HFIP).

The solvent is chosen such that there is the proper balance of viscosity, deposition level of the polymer, solubility of the pharmaceutical agent, wetting of the stent, and evaporation rate of the solvent to properly coat the stent. In a preferred embodiment, the drug and the polymer are both soluble in the solvent. In certain instances, the coating polymer is soluble in the solvent and the drug is dispersed in the polymer solution. In this case, the solvent should suspend the drug without causing it to aggregate or agglomerate. Mixed solvent systems can also be used to control viscosity and evaporation rates. Further, the solvent should not react with or inactivate the drug or react with the polymer. Suitable solvents include, without limitation, acetone, N-methylpyrrolidone (NMP), dimethyl sulfoxide (DMSO), toluene, methylene chloride, chloroform, 1,1,2-trichloroethane (TCE), various freons, dioxane, ethyl acetate, tetrahydrofuran (THF), dimethylformamide (DMF), dimethylacetamide (DMAC), and combinations thereof.

Generally, the amount of polymer coating to be placed on the stent will vary, for example, depending on the polymer, the drug, and the design of the stent. For instance, the amount of coating can range from between about 0.1% to about 30% of the total weight of the stent after coating, preferably between about 0.5% to about 20%. The polymer coating can be applied in one or more coating steps depending on the amount of polymer to be applied. Different polymers may also be used for different layers in the stent coating. Such layers can contain the same drug or different drugs. For example, it is advantageous to use a dilute first coating solution of a polymer to promote adhesion of subsequent coating layers that contain the drug.

Additionally, a top coating can be applied to delay release of the drug, or alternatively, can be used as a matrix for the delivery of a different drug. Coating the stent with layers of fast and slow hydrolyzing polymers can be used to stage the release of the drug or to control the release of different drugs placed in different layers. Polymer blends may also be used to control the release rate of the drug or combination of drugs or to provide a desirable balance of coating (e.g., elasticity, toughness, etc.) and drug delivery characteristics (e.g., release profile). Polymers with different solubilities in solvents can be used to build up different polymer layers that may be used to deliver different drugs or control the release profile of a drug. Multiple layers of different drugs could be provided by alternating layers of first one polymer and then another. Those skilled in the art will appreciate numerous other layering approaches that can be used to provide the desired drug delivery profile.

The polymer coatings on the drug-eluting stents of the present invention are suitable for delivering drugs including, without limitation, protein kinase inhibitors, antiproliferative/antimitotic agents (e.g., vinblastine, vincristine, vinorelbine, mechlorethamine, cyclophosphamide and analogs, melphalan, chlorambucil), paclitaxel, epipidophyllotoxins (e.g., etoposide, teniposide), antibiotics (e.g., rapamycin, dactinomycin, daunorubicin, doxorubicin, idarubicin), anthracyclines, mitoxantrone, bleomycins, plicamycin, mitomycin, enzymes (e.g., L-asparaginase), ethylenimines and methylmelamines (e.g., hexamethylmelamine and thiotepa), alkyl sulfonate-busulfans, nirtosoureas (e.g., carmustine and analogs, streptozocin), trazenes-dacarbazinine (e.g., DTIC); antimetabolites (e.g., methotrexate), pyrimidine analogs (e.g., fluorouracil, floxuridine, and cytarabine), purine analogs and related inhibitors (e.g., mercaptopurine, thioguanine, pentostatin, 2-chlorodeoxyadenosine), platinum coordination complexes (e.g., cisplatin, carboplatin), procarbazine, hydroxyurea, mitotane, aminoglutethimide, hormones, anticoagulants (e.g., heparin, synthetic heparin salts and other inhibitors of thrombin), fibrinolytic agents (e.g., tissue plasminogen activator, streptokinase, urokinase), antiplatelet agents (e.g., aspirin, dipyridamole, ticlopidine, clopidogrel, abciximab), antimigratory agents, antisecretory agents (e.g., breveldin), anti-inflammatory agents (e.g., cortisol, cortisone, fludrocortisone, prednisone, prednisolone, 6-α-methylprednisolone, triamcinolone, betamethasone, dexamethasone), non-steroidal agents (e.g., salicylic acid and derivatives thereof, para-aminophenol derivatives such as acetaminophen), indole and indene acetic acids (e.g., indomethacin, sulindac, and etodalac), heteroaryl acetic acids (e.g., tolmetin, diclofenac, and ketorolac), arylpropionic acids (e.g., ibuprofen and derivatives thereof), anthranilic acids (e.g., mefenamic acid, meclofenamic acid), enolic acids piroxicam, tenoxicam, phenylbutazone, oxyphenthatrazone), nabumetone, gold compounds (e.g., auranofin, aurothioglucose, gold sodium thiomalate), immunosuppressive agents (e.g., cyclosporine, tacrolimus (FK-506), sirolimus (rapamycin), azathioprine, mycophenolate mofetil), angiogenic agents (e.g., vascular endothelial growth factor (VEGF), fibroblast growth factor (FGF)), nitric oxide donors, antisense olgionucleotides, and combinations thereof.

In a preferred embodiment of the present invention, the drug is a protein kinase inhibitor. In a particularly preferred embodiment, the drug is an inhibitor of the Syk protein tyrosine kinase. Suitable Syk inhibitors include, without limitation, NVP-QAB205 (Novartis); purine-2-benzamine derivatives such as those described in U.S. Pat. No. 6,589,950; pyrimidine-5-carboxamide derivatives such as those described in PCT Publication No. WO 99/31073; 1,6-naphthyridine derivatives such as those described in U.S. Pat. Publication No. 2003/0229090; BAY 61-3606 (Bayer); piceatannol; 3,4-dimethyl-10-(3-aminopropyl)-9-acridone oxalate); and combinations thereof.

In another preferred embodiment of the present invention, the drug-eluting stents contain a combination of a Syk inhibitor and at least one additional drug. Suitable drugs include, without limitation, drugs such as those described above. In a particularly preferred embodiment, the drug-eluting stents contain a combination of a Syk inhibitor and rapamycin. Suitable amounts of the drug or drug combination for use in the present invention range from between about 0.001% to about 70%, preferably from about 0.001% to about 50%, more preferably from about 0.001% to about 30%, and most preferably from about 0.001% to about 20%, by weight of the coating.

The spleen tyrosine kinase (Syk) family of protein tyrosine kinases is essential for hematopoeitic cell development and for signaling through the T-cell and B-cell antigen receptors as well as the IgG and IgE Fc receptors. For example, members of the Syk family, including Syk and Zap-70, are involved in the normal development and function of the immune system, and Syk is required for the maintenance of vascular integrity. In leukocytes, Syk is activated by binding to di-phosphorylated immune receptor tyrosine-based activation motifs (pITAMs; Chu et al., *Immunol Rev.*, 165:167-180 (1998)). Syk can also be activated by integrin adhesion receptors. These kinases are structurally distinct in that they contain tandem N-terminal SH2 domains followed by a C-terminal kinase domain. A helical "Y" shaped linker region termed "interdomain A" joins the tandem SH2 domains. Kinase activity and subcellular localization within immune cells can be controlled by the binding of its tandem SH2 domains to di-phosphorylated immune receptor tyrosine-based activation motifs. Linking the tandem SH2 domains with the kinase domain is the "interdomain B" region. This region contains a number of tyrosines that are phosphorylated in vivo and can recruit other signaling/adaptor molecules such as Src family members.

The coating can be formulated by mixing one or more drugs, e.g., Syk inhibtors, with the coating polymers in a coating mixture. The drug can be present as a liquid, a solid, or any other appropriate physical form. Optionally, the mixture can include one or more additives, e.g., nontoxic auxiliary substances such as diluents, carriers, excipients, stabilizers, and the like. For example, a biocompatible hydrophilic polymer can be added to a biocompatible hydrophobic coating to modify the release profile of the drug. More particularly, a hydrophilic polymer such as polyethylene oxide, polyvinyl pyrrolidone, polyethylene glycol, carboxylmethyl cellulose, hydroxymethyl cellulose and combinations thereof can be added to an aliphatic polyester coating to modify the release profile of the drug.

Once prepared, the polymer/drug mixture can be applied to the surfaces of the stent by any technique known in the art, such as dip coating, spray coating, brush coating, dip/spin coating, or combinations thereof. The solvent is allowed to evaporate, leaving a polymer film containing the drug. One skilled in the art will appreciate other methods for applying the polymer/drug mixture to the stent.

Bioabsorbable polymers, upon contact with body fluids including blood and the like, undergo gradual degradation (e.g., hydrolysis) with concomitant release of the drug for a sustained or extended period of time. Both non-bioabsorbable and bioabsorbable polymers release the drug by diffusion. Such release can result in prolonged delivery (e.g., from about 1 to about 2,000 hours, preferably from about 2 to about 800 hours) of effective amounts (e.g., from about 0.001 $\mu g/cm^2$-min to about 100 $\mu g/cm^2$-min) of the drug.

Individual formulations of drugs and polymers may be tested in appropriate in vitro and in vivo models to achieve the desired drug release profiles. For example, a drug could be formulated with a polymer (or polymer blend) coated on a stent and placed into an agitated or circulating fluid system (e.g., PBS containing 4% bovine serum albumin). Samples of the circulating fluid could then be taken to determine the release profile (e.g., by HPLC). The release of the drug from the stent coating into the interior wall of a lumen could be modeled, for example, in an appropriate animal model system. The drug release profile could then be monitored by appropriate means, such as, for example, by taking samples at specific times and assaying the samples for drug concentration (e.g., by HPLC). Thrombus formation can be modeled in animal models using the $^{111}$In-platelet imaging methods known to those skilled in the art.

In addition to drug-eluting stents, drug-coated stents where the drug is placed in reservoirs, channels, or micropores on the stent body are suitable for use in the present invention. For example, the stent can contain reservoirs or channels which can be loaded with the drug. A biocompatable polymer coating or membrane can then be applied over the reservoirs or channels to control the diffusion of the drug into the vessel wall. One advantage of this system is that the properties of the polymer coating or membrane can be optimized for achieving superior biocompatibility and adhesion, without the additional requirement of being able to load and release the drug. The size, shape, position, and number of reservoirs can be used to control the amount of drug, and therefore the dose delivered.

For example, a stent, whose body has been modified to contain reservoirs, channels, or micropores, is dipped into a drug solution in an organic solvent such as acetone or methylene chloride for a period of time sufficient to allow the drug solution to permeate into the reservoirs, channels, or micropores on the stent body. After the solvent has been allowed to evaporate, the stent is dipped briefly in fresh solvent to remove excess surface-bound drug. A polymer solution is then applied to the stent as described above. This outer layer of polymer acts as a coating or membrane to control the diffusion of the drug.

The drug can also be either covalently or ionically bonded to an intravascular device, such as a stent. More particularly, the drug can be bonded directly to the stent or bonded via a spacer group or linker. For covalent attachment, it is preferred that a polymer-coated stent be used and that the drug, e.g., Syk inhibitor, be covalently bonded to the stent via a spacer group or linker having a chain length of from 1 to 250 atoms. For example, the spacer group may include an alkyl, alkylamine, oxygenated polyolefin, aliphatic polyester, polyamino acid, polyamine, hydrophilic polysiloxane, hydrophilic polysilazane, hydrophilic acrylate, hydrophilic methacrylate, linear and lightly branched polysaccharide, and the like. Further, the spacer group can contain a hydrolytically or enzymatically labile covalent bond such that the drug can be released from the stent upon cleavage by an endogenous or exogenous protease.

V. METHODS OF ADMINISTRATION

In one embodiment, the present invention provides methods for inhibiting restenosis, thrombosis, and/or inflammation in a patient undergoing a vascular intervention by treating the patient with an intravascular device coated with a Syk inhibitor. Examples of intravascular devices include, without limitation, stents, balloon catheters, autologous venous/arterial grafts, prosthetic venous/arterial grafts, vascular catheters, and vascular shunts. In a preferred embodiment, the intravascular device is a stent coated with a Syk inhibitor. One skilled in the art will readily appreciate procedures suitable for implanting the intravascular device into a vessel of a patient.

In another embodiment, the present invention provides methods for treating sickle cell disease using Syk inhibitors. Sickle cell disease refers to an inherited disorder of the red blood cells in which one hemoglobin allele encodes the sickle hemoglobin (S) protein, and the other allele encodes another unusual hemoglobin protein, such as hemoglobin (S), (C), (D), (E), and (βThal). The most common types of sickle cell disease include sickle cell anemia, sickle-hemoglobin C disease, sickle beta-plus thalassemia, and sickle beta-zero thalassemia.

When sickle-shaped cells block small blood vessels, less blood can reach that part of the body. Tissue that does not receive normal blood flow eventually becomes damaged, causing the complications of sickle cell disease. While normal red blood cells contain hemoglobin A, sickle-shaped cells contain abnormal types of hemoglobin such as hemoglobin (S), (C), (D), (E), and (βThal). Normal red blood cells are soft and round and can squeeze through tiny blood vessels. Typically, normal red blood cells live for about 120 days before new ones replace them. However, patients with sickle cell disease have red blood cells containing abnormal types of hemoglobin and do not live as long as normal red blood cells (e.g., about 16 days). They also become stiff, distorted in shape, and have difficulty passing through the body's small blood vessels.

Sickle-shaped cells are destroyed rapidly in the body of patients with sickle cell disease, causing anemia, jaundice, and the formation of gallstones. Sickle-shaped cells also cause damage to most organs, including the spleen, kidneys, and liver. Damage to the spleen makes sickle cell disease patients, especially young children, easily overwhelmed by certain bacterial infections. In addition, sickle-shaped cells block the flow of blood through vessels resulting in lung tissue damage (acute chest syndrome), pain episodes (arms, legs, chest, and abdomen), stroke, and priapism (painful prolonged erection). The generation of vascular occlusion is mediated by the P-selectin-dependent recruitment and adhesion of sickle cells to the vascular endothelium. As a result, interactions between sickle cells and endothelial cells lead to crises in patients with sickle cell disease such as vascular occlusion. The present invention provides methods for treating sickle cell disease using Syk inhibitors that block the adhesion of sickle cells to the vascular endothelium, thereby overcoming such crises in patients with sickle cell disease.

Current treatment options for patients with sickle cell disease include antibiotics, pain management, intravenous fluids, blood transfusion, surgery, and compounds such as hydroxyurea. However, all of these options suffer from one or more significant drawbacks, including, without limitation, producing unwanted side-effects, being an ineffective procedure, being a costly procedure, being an invasive procedure, being ineffective at reducing the frequency of severe pain, being ineffective at reducing acute chest syndrome, and requiring blood transfusions. The present invention provides methods for treating sickle cell disease using Syk inhibitors that overcome some or all of the drawbacks and limitations of current treatment options.

Administration of a composition comprising one or more Syk inhibitors for treating sickle cell disease with one or more suitable pharmaceutical excipients as necessary can be carried out via any of the accepted modes of administration. Thus, administration can be, for example, oral, topical, intravenous, subcutaneous, transcutaneous, transdermal, intramuscular, intra-joint, parenteral, intra-arteriole, intradermal, intraventricular, intracranial, intraperitoneal, intralesional, intranasal, rectal, vaginal, or by inhalation.

The compositions of the present invention containing one or more Syk inhibitors can be administered repeatedly, e.g., at least 2, 3, 4, 5, 6, 7, 8, or more times, or the composition may be administered by continuous infusion. Suitable sites of administration include, but are not limited to, skin, bronchial, gastrointestinal, anal, vaginal, eye, and ear. The formulations may take the form of solid, semi-solid, lyophilized powder, or liquid dosage forms, such as, for example, tablets, pills, capsules, powders, solutions, suspensions, emulsions, suppositories, retention enemas, creams, ointments, lotions, gels, aerosols, or the like, preferably in unit dosage forms suitable for simple administration of precise dosages.

The term "unit dosage form" refers to physically discrete units suitable as unitary dosages for human subjects and other mammals, each unit containing a predetermined quantity of drug calculated to produce the desired onset, tolerability, and/or therapeutic effects, in association with a suitable pharmaceutical excipient (e.g., an ampoule). In addition, more concentrated compositions may be prepared, from which the more dilute unit dosage compositions may then be produced. The more concentrated compositions thus will contain substantially more than, e.g., at least 1, 2, 3, 4, 5, 6, 7, 8, 9, 10, or more times the amount of one or more Syk inhibitors.

Methods for preparing such dosage forms are known to those skilled in the art (see, for example, REMINGTON'S PHARMACEUTICAL SCIENCES, 18TH ED., Mack Publishing Co., Easton, Pa. (1990)). In addition, pharmaceutically acceptable salts of the Syk inhibitors of the present invention (e.g., acid addition salts) may be prepared and included in the compositions using standard procedures known to those skilled in the art of synthetic organic chemistry and described, e.g., by J. March, Advanced Organic Chemistry: Reactions, Mechanisms and Structure, $4^{th}$ Ed. (New York: Wiley-Interscience, 1992). As used herein, the term "pharmaceutically acceptable salts" refers to any acid or base addition salt whose counter-ions are non-toxic to the patient in pharmaceutical doses of the salts. A host of pharmaceutically acceptable salts are well known in the pharmaceutical field. For example, pharmaceutically acceptable acid addition salts include, without limitation, those derived from mineral acids and organic acids such as hydrohalides (e.g., hydrochlorides and hydrobromides), sulphates, phosphates, nitrates, sulphamates, acetates, citrates, lactates, tartrates, malonates, oxalates, salicylates, propionates, succinates, fumarates, maleates, methylene-bis-b-hydroxynaphthoates, gentisates, isethionates, di-p-toluoyltartrates, methane-sulphonates, ethanesulphonates, benzenesulphonates, p-toluenesulphonates, cyclohexylsulphamates, quinates, and the like. Pharmaceutically acceptable base addition salts include, without limitation, those derived from alkali or alkaline earth metal bases or conventional organic bases, such as triethylamine, pyridine, piperidine, morpholine, N-methylmorpholine, and the like.

The compositions typically include a conventional pharmaceutical carrier or excipient and may additionally include other medicinal agents, carriers, adjuvants, diluents, tissue permeation enhancers, solubilizers, and the like. Preferably, the composition will contain about 0.01% to about 90%, preferably about 0.1% to about 75%, more preferably about 0.1% to 50%, still more preferably about 0.1% to 10% by weight of one or more Syk inhibitors, with the remainder consisting of suitable pharmaceutical carrier and/or excipients. Appropriate excipients can be tailored to the particular composition and route of administration by methods well known in the art, e.g., REMINGTON'S PHARMACEUTICAL SCIENCES, supra.

Examples of suitable excipients include, but are not limited to, lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, and polyacrylic acids such as Carbopols. The compositions can additionally include lubricating agents such as talc, magnesium stearate, and mineral oil; wetting agents; emulsifying agents; suspending agents; preserving agents such as methyl-, ethyl-, and propyl-hydroxy-benzoates; pH adjusting agents such as inorganic and organic acids and bases; sweetening agents; and flavoring agents.

For oral administration, the compositions can be in the form of tablets, capsules, cachets, emulsions, suspensions, solutions, syrups, elixirs, sprays, boluses, lozenges, powders, granules, and sustained-release formulations. Suitable excipients for oral administration include pharmaceutical grades of mannitol, lactose, starch, magnesium stearate, sodium saccharine, talcum, cellulose, glucose, gelatin, sucrose, magnesium carbonate, and the like.

In some embodiments, the compositions take the form of a pill, tablet, or capsule, and thus, the composition can contain, along with one or more Syk inhibitors, a diluent such as lactose, sucrose, dicalcium phosphate, and the like; a disintegrant such as starch or derivatives thereof; a lubricant such as magnesium stearate and the like; and/or a binder such a starch, gum acacia, polyvinylpyrrolidone, gelatin, cellulose and derivatives thereof. A tablet can be made by any compression or molding process known to those of skill in the art. Compressed tablets may be prepared by compressing in a suitable machine the Syk inhibitors in a free-flowing form, e.g., a powder or granules, optionally mixed with accessory ingredients, e.g., binders, lubricants, diluents, disintegrants, or dispersing agents. Molded tablets can be made by molding in a suitable machine a mixture of the powdered Syk inhibitors with any suitable carrier.

The Syk inhibitors can also be formulated into a suppository disposed, for example, in a carrier containing polyethylene glycol (PEG), hard fat, and/or hydrogenated cocoglyceride. Compositions suitable for rectal administration may also comprise a rectal enema unit containing one or more Syk inhibitors and pharmaceutically-acceptable vehicles (e.g., 50% aqueous ethanol or an aqueous salt solution) that are physiologically compatible with the rectum and/or colon. The rectal enema unit contains an applicator tip protected by an inert cover, preferably comprised of polyethylene, lubricated with a lubricant such as white petrolatum, and preferably protected by a one-way valve to prevent back-flow of the dispensed formula. The rectal enema unit is also of sufficient length, preferably two inches, to be inserted into the colon via the anus.

Liquid compositions can be prepared by dissolving or dispersing one or more Syk inhibitors and optionally one or more pharmaceutically acceptable adjuvants in a carrier such as, for example, aqueous saline, aqueous dextrose, glycerol, ethanol, and the like, to form a solution or suspension, e.g., for oral, topical, or intravenous administration. For topical administration, the composition containing one or more Syk inhibitors can be in the form of emulsions, lotions, gels, foams, creams, jellies, solutions, suspensions, ointments, and transdermal patches. For delivery by inhalation, the compositions can be delivered as a dry powder or in liquid form via a nebulizer. For parenteral administration, the compositions can be in the form of sterile injectable solutions and sterile packaged powders. Preferably, injectable solutions are formulated at a pH of about 4.5 to about 7.5.

The compositions of the present invention can also be provided in a lyophilized form. Such compositions may include a buffer, e.g., bicarbonate, for reconstitution prior to administration, or the buffer may be included in the lyophilized composition for reconstitution with, e.g., water. The lyophilized composition may further comprise a suitable vasoconstrictor, e.g., epinephrine. The lyophilized composition can be provided in a syringe, optionally packaged in combination with the buffer for reconstitution, such that the reconstituted composition can be immediately administered to a patient.

VI. EXAMPLES

The following examples are offered to illustrate, but not to limit, the claimed invention.

Example 1

The Effect of Syk Gene Targeting on Platelet Thrombus Formation

Figure 1:
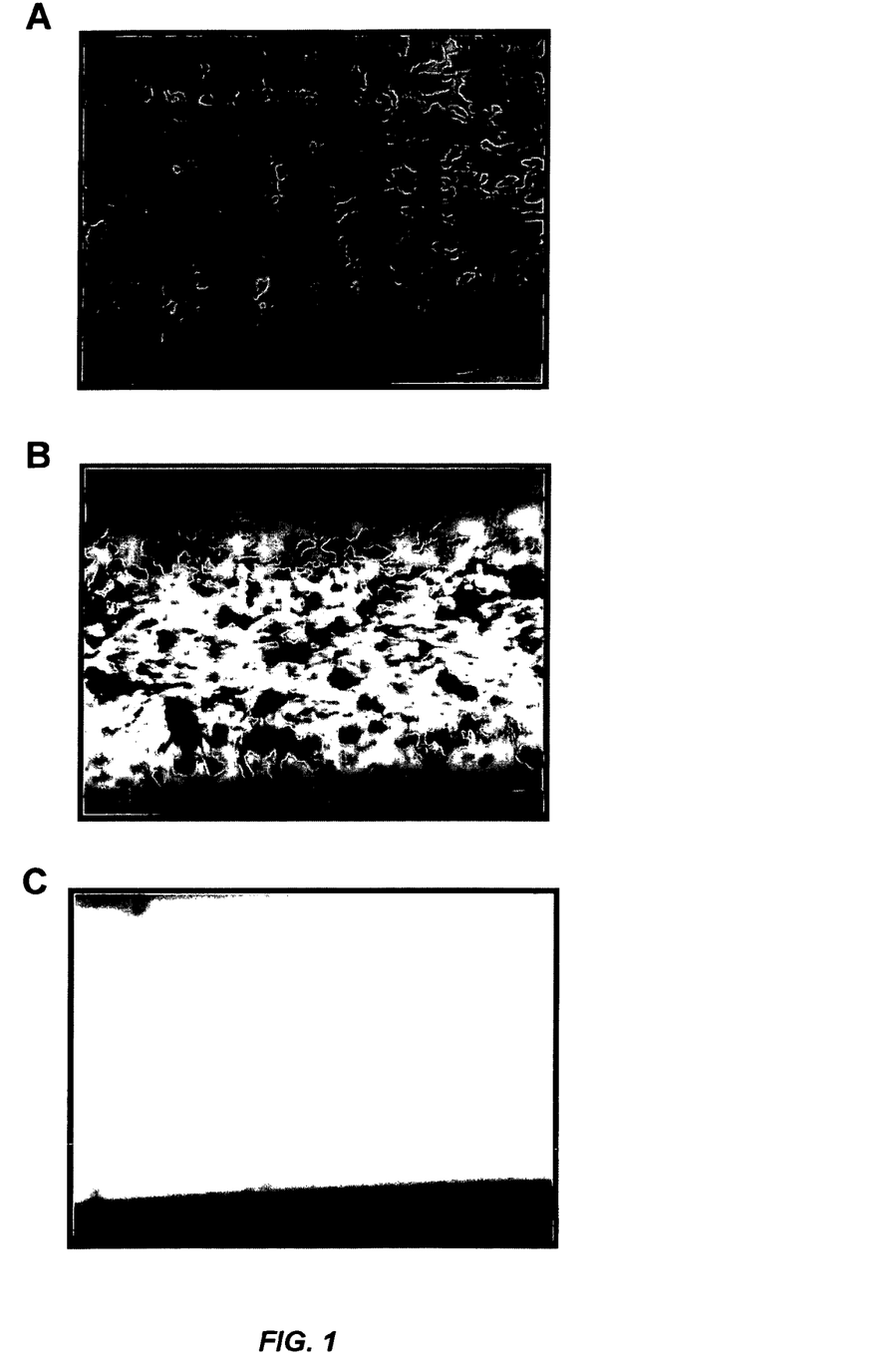
FIG. 1 shows the effect of Syk gene targeting on platelet thrombus formation.

FIG. 1 illustrates the effect of anticoagulated whole blood taken from wild-type (A), Syk+/− (B), or Syk−/− (C) mice on platelet thrombus formation. Briefly, whole blood was exposed to type III collagen for 2.5 minutes at a rate of shear equivalent to that encountered in coronary arteries. FIG. 1A shows the robust thrombus formation that occurred using wild-type blood. However, thrombus formation was completely absent using blood from Syk−/− mice (FIG. 1C), indicating that Syk−/− platelets were defective in platelet adhesion to type III collagen at these rates of shear. Thrombus formation was also defective in the blood from Syk+/− mice (FIG. 1B). These findings indicate that partial (Syk+/−) or complete (Syk−/−) inhibition of Syk blocks platelet adhesion and provides a significant inhibition of thrombosis on collagen-coated surfaces under conditions of shear similar to those encountered in coronary arteries.

Example 2

Figure 2:
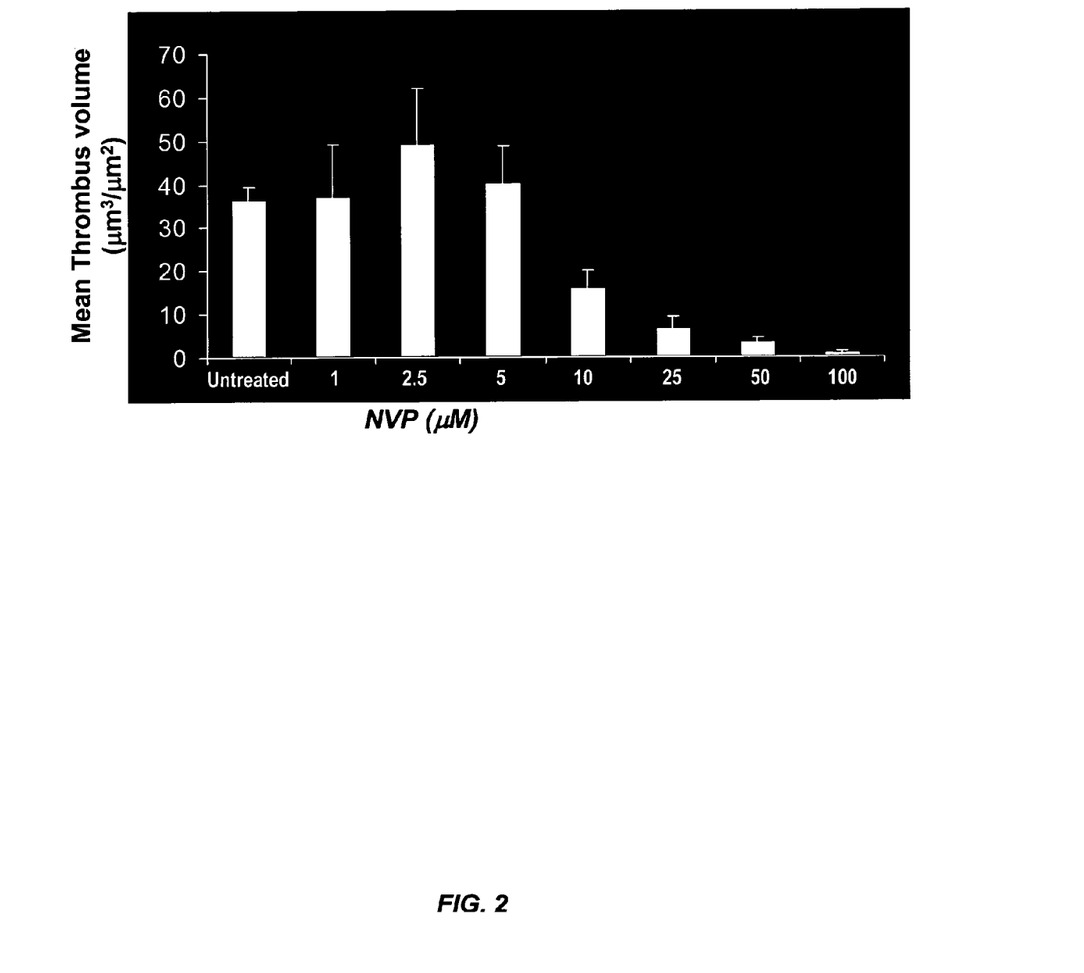
FIG. 2 shows the effect of inhibition of the tyrosine kinase activity of Syk on platelet thrombus formation.

The Effect of Inhibition of the Tyrosine Kinase Activity of Syk on Platelet Thrombus Formation FIG. 2 illustrates that increasing concentrations of NVP-QAB205, an inhibitor of the tyrosine kinase activity of Syk, caused inhibition of thrombus formation. Briefly, unanticoagulated human blood was exposed to type III collagen for 4 minutes at a rate of shear (e.g., about 850/sec.) equivalent to that encountered in coronary arteries.

Example 3

Figure 3:
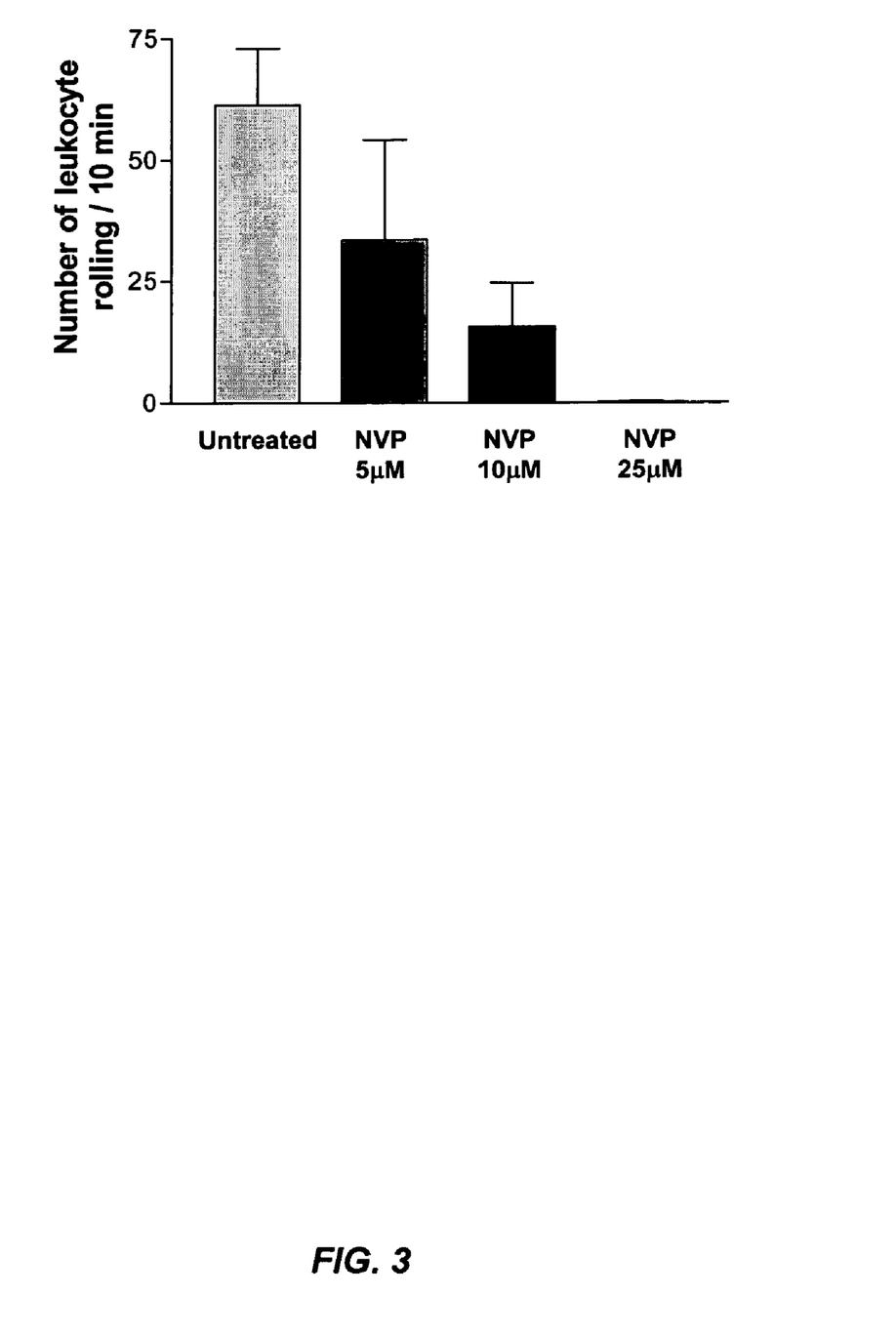
FIG. 3 shows the effect of inhibition of the tyrosine kinase activity of Syk on the recruitment of leukocytes to adherent, activated platelets.

The Effect of Inhibition of the Tyrosine Kinase Activity of Syk on the Recruitment of Leukocytes to Adherent, Activated Platelets FIG. 3 illustrates that increasing concentrations of NVP-QAB205 caused inhibition of leukocyte rolling, even at concentrations that did not completely block platelet adhesion (e.g., at 5, 10, and 25 μM of NVP-QAB205; see, FIG. 2). Briefly, human blood, anticoagulated with citrate in the presence of 2.5 μM Integrilin, was exposed for 10 minutes to type III collagen at a shear rate of 650/sec. These findings show that Syk inhibition blocks leukocyte adhesion to activated, collagen-adhering platelets.

Example 4

Figure 4:
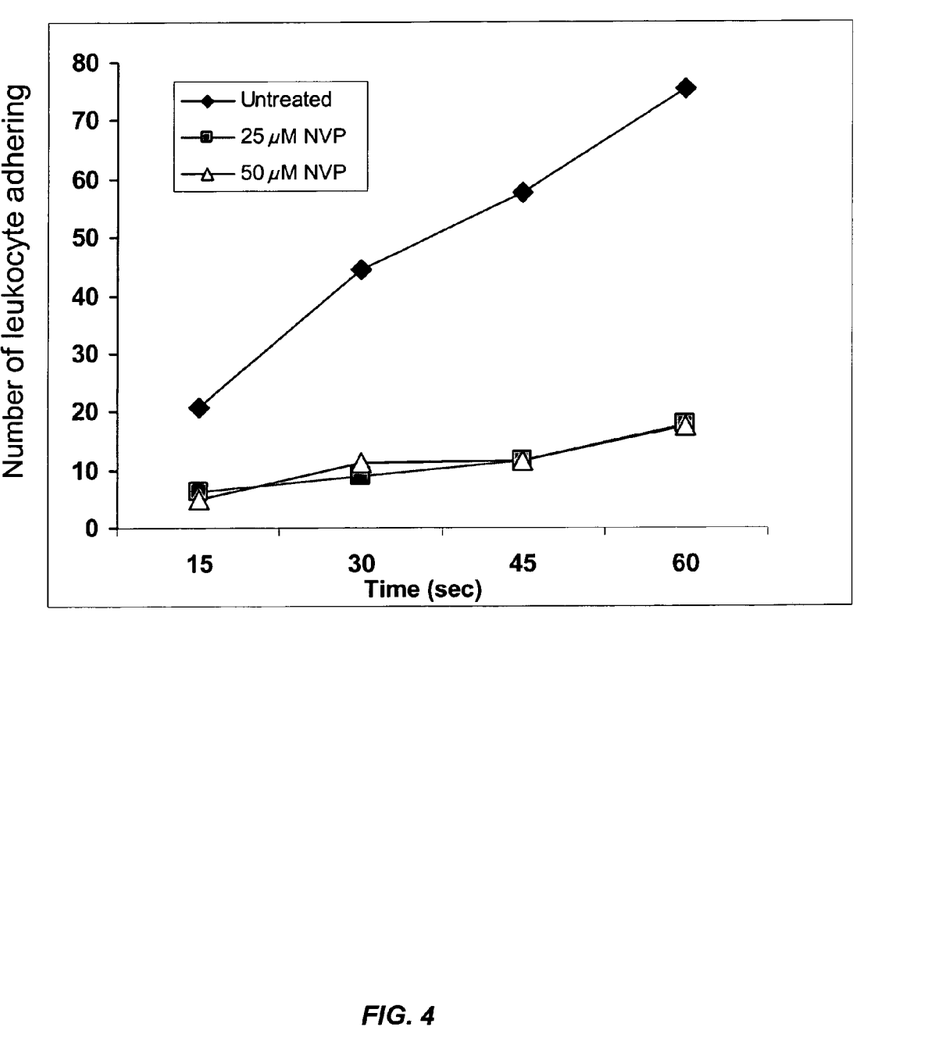
FIG. 4 shows the effect of inhibition of the tyrosine kinase activity of Syk on the recruitment of leukocytes to activated endothelial cells.

The Effect of Inhibition of the Tyrosine Kinase Activity of Syk on the Recruitment of Leukocytes to Activated Endothelial Cells FIG. 4 illustrates that NVP-QAB205, at a concentration of either 25 or 50 μM, provided marked inhibition of leukocyte adhesion to activated endothelial cells. Briefly, cultured monolayers of human umbilical endothelial cells were activated by exposure to IL-1 β for 24 hrs. Human blood, anticoagulated with citrate, was exposed to the activated endothelial cells at a shear rate of 650/sec for the time indicated.

All publications and patent applications cited in this specification are herein incorporated by reference as if each individual publication or patent application were specifically and individually indicated to be incorporated by reference. Although the foregoing invention has been described in some detail by way of illustration and example for purposes of clarity of understanding, it will be readily apparent to those of ordinary skill in the art in light of the teachings of this invention that certain changes and modifications may be made thereto without departing from the spirit or scope of the appended claims.

What is claimed is:

1. An intravascular device having a coating, said coating comprising a polymer and a spleen tyrosine kinase (Syk) inhibitor, wherein said Syk inhibitor is selected from the group consisting of a purine-2-benzamine derivative, a pyrimidine-5-carboxamide derivative, a 1,6-naphthyridine derivative, BAY 61-3606, piceatannol, 3,4-dimethyl-10-(3-aminopropyl)-9-acridone oxalate), and combinations thereof; and wherein said coating is applied to said intravascular device, wherein said spleen tyrosine kinase (Syk) inhibitor is present in an amount sufficient to inhibit restenosis, thrombosis, and inflammation in a patient undergoing a vascular intervention.

2. The intravascular device of claim 1, wherein said intravascular device is selected from the group consisting of a stent, a balloon catheter, an autologous venous/arterial graft, a prosthetic venous/arterial graft, a vascular catheter, and a vascular shunt.

3. The intravascular device of claim 2, wherein said intravascular device is a stent.

4. The intravascular device of claim 1, wherein said polymer is selected from the group consisting of a bioabsorbable polymer, a biostable polymer, and combinations thereof.

5. The intravascular device of claim 4, wherein said bioabsorbable polymer is selected from the group consisting of aliphatic polyesters, poly(amino acids), poly(ether-ester) copolymers, polyalkylene oxalates, polyanhydrides, polysaccharides, polyamides, poly(iminocarbonates), polyorthoesters, polyoxaesters, polyamidoesters, polyoxaesters containing amido groups, polyphosphazenes, and combinations thereof.

6. The intravascular device of claim 4, wherein said biostable polymer is selected from the group consisting of polyurethanes, silicones, polymethacrylates, poly(ethylene-vinylacetates), polyesters, polyalkyl oxides, polyvinyl alcohols, polyethylene glycols, polyvinyl pyrrolidone, polyolefins, polyisobutylene and ethylene-α-olefin copolymers, acrylic polymers and copolymers, vinyl halide polymers and copolymers, polyvinyl ethers, polyvinylidene halides, polyacrylonitriles, polyvinyl ketones, polyvinyl aromatics, polyvinyl esters, copolymers of vinyl monomers, acrylonitrile-styrene copolymers, acrylonitrile-butadiene-styrene copolymers, ethylene-vinyl acetate copolymers, polyamides, alkyl resins, polycarbonates, polyoxymethylenes, polyimides, polyethers, epoxy resins, rayon, rayon-triacetate, cellulose esters, cellulose acetate, cellulose acetate butyrate, cellophane, cellulose nitrate, cellulose propionate, cellulose ethers, and combinations thereof.

7. The intravascular device of claim 1, wherein said Syk inhibitor is released from said intravascular device.

8. The intravascular device of claim 1, wherein said Syk inhibitor is covalently attached to said intravascular device.

9. The intravascular device of claim 1, wherein said coating contains one or more additional drugs.

10. The intravascular device of claim 9, wherein said one or more additional drugs are selected from the group consisting of protein kinase inhibitors, antiproliferative agents, antimitotic agents, antibiotics, antimetabolites, pyrimidine analogs, purine analogs, anticoagulants, fibrinolytic agents, antiplatelet agents, antimigratory agents, antisecretory agents, anti-inflammatory agents, non-steroidal agents, immunosuppressive agents, angiogenic agents, and combinations thereof.

11. The intravascular device of claim 10, wherein said antibiotic is rapamycin.

12. The intravascular device of claim 1, wherein said coating is applied by dip coating.

13. The intravascular device of claim 1, wherein said coating is applied by spray coating.

* * * * *